(12) United States Patent
Ponzone et al.

(10) Patent No.: US 6,911,325 B1
(45) Date of Patent: Jun. 28, 2005

(54) **PROCESS FOR THE PREPARATION OF DERIVATIVES OF *RUSCUS ACULEATUS* STEROID GLYCOSIDES BY ENZYMATIC HYDROLYSIS**

(75) Inventors: Cesare Ponzone, Milan (IT); Mario De Rosa, Naples (IT); Alessandra Morana, Naples (IT); Antonella Di Lazzaro, Portici (IT)

(73) Assignee: Indena S.p.A., Milan (IT)

( * ) Notice: Subject to any disclaimer, the term of this patent is extended or adjusted under 35 U.S.C. 154(b) by 0 days.

(21) Appl. No.: 09/979,106

(22) PCT Filed: May 29, 2000

(86) PCT No.: PCT/EP00/04873

§ 371 (c)(1),
(2), (4) Date: Nov. 19, 2001

(87) PCT Pub. No.: WO00/73483

PCT Pub. Date: Dec. 7, 2000

(30) Foreign Application Priority Data

Jun. 1, 1999 (IT) ..................... MI99A001222

(51) Int. Cl.[7] ............................... C12P 19/44
(52) U.S. Cl. ............................. 435/74; 435/53; 435/72; 435/99; 536/4.1; 536/4.4; 536/6; 536/6.1; 536/6.3

(58) Field of Search .................... 536/4.4, 4.1, 6.3, 536/6.1, 6; 435/53, 74, 72, 99

(56) References Cited

FOREIGN PATENT DOCUMENTS

| DE | 22 02 393 | | 9/1972 |
|---|---|---|---|
| GB | 1 380 253 | * | 1/1975 |

OTHER PUBLICATIONS

Caldini et al, Enzyme Microb. Technol. 16:286–291 (1994).*

Perepelitsa, E.D. et al., "Usloviya passhepleniya fermentnim preparatom *Aspergillus niger* BKMT–33 protodiostsina–osnobnogo glikozida iz Tribulus terrestris L." Prikladnaya Biokhimiya I Mikrobiologiya, vol. 11, No. 6, pp. 901–905, 1975.

* cited by examiner

*Primary Examiner*—Francisco Prats
(74) *Attorney, Agent, or Firm*—Jones Day

(57) ABSTRACT

A process for the preparation of desglucodesrhamnoruscin which comprises the enzymatic hydrolysis of *Ruscus Aculeatus* steroid glycosides (ruscosaponins) by means of crude hydrolases from *aspergillus niger*.

9 Claims, No Drawings

PROCESS FOR THE PREPARATION OF DERIVATIVES OF *RUSCUS ACULEATUS* STEROID GLYCOSIDES BY ENZYMATIC HYDROLYSIS

TECHNICAL FIELD

The present invention relates to a process for the preparation of derivatives of *Ruscus Aculeatus* steroid glycosides (ruscosaponins).

More particularly, the invention relates to a process for the preparation of desglucodesrhamnoruscin by partial enzymatic hydrolysis of ruscin, desglucoruscin or ruscoside.

SUMMARY OF THE INVENTION

The enzymatic hydrolysis according to the invention is carried out by the means of crude enzyme preparations based on hydrolases extracted from *Aspergillus niger*. Said preparations are commercially available and are used in the wine and alimentary industries. Particularly preferred is the use of the preparation commercially available from Gist Brocades under the trademark Cytolase PCL5.

Said enzyme preparations have at the same time β-glucopyranosidase and α-rhamnopyranosidase activities and therefore provide the sequential removal of the β-glucoside residue followed by removal of the α-rhamnoside residue to the desired product.

DETAILED DESCRIPTION OF THE PREFERRED EMBODIMENTS

The enzymatic hydrolysis is carried out in aqueous solution buffered to pH 5 or in water containing up to about 30% by volume of ethanol. It has been observed that in practice the presence of ethanol does not adversely affect the enzymatic activity: the β-glucopyranosidase activity increases in the presence of ethanol whereas, on the other hand, the α-rhamnopyranosidase activity slightly decreases, but to a degree which anyhow does not affect the reaction of the invention. An about 30% v/v ethanol percentage is necessary for the complete solubilization of desglucoruscin, whereas lower percentages, of about 17% v/v, are required for the ruscoside. The use of the latter can therefore be sometimes preferred also in that it requires no specific pre-treatments and due to its surface active properties solubilize the desglucoruscin resulting from the first step of the hydrolysis enzymatic, which can then be transformed into α-rhamnopiranosidase more efficiently.

The concentration of ruscosaponin can range from about 5 to about 40% w/v, and the hydrolysis is carried out at temperatures ranging from 20 to 50° C. for times ranging from 3 to 7 days.

At the end of the bioconversion process, the final desglucodesrhamnoruscin product, insoluble in the reaction system, can be easily recovered by centrifugation and subsequent washing with methanol. Furthermore, the process of the invention can be carried out continuously, removing the hydrolysed product at fixed times and continuously adding fresh substrate, thanks to the stability of the enzymes used. For this purpose, a bioreactor equipped with an ultrafiltration membrane, to avoid the accumulation of inhibitors and denaturating molecules, will be preferably used.

The following example illustrates the invention in greater detail.

EXAMPLE

The enzymatic preparation Cytolase PCL5 (Gist Brocades) was diafiltered before use against 0.1 M citrate-phosphate buffer pH 5 in Amicon apparatus equipped with a XM membrane (cut-off 50 kDa) in order to remove denaturating agents and inhibitors.

The incubation mixture was prepared by adding in the following order: substrate (desglucoruscin or ruscoside), 0.1 M citrate-phosphate buffer pH 5.0, Cytolase PCL5 and slowly, under stirring, ethanol. The substrate concentration varied from 5 to 40% (w/v) and the ethanol concentration from 0 to 30% (v/w). The reaction was followed by TLC on silica gel plates (60 P250 Merck) with ethyl acetate/methanol/water 100:15:10 as eluent. The activation of the enzymatic preparation was of 38 units of β-glucopyranosidase and of 2.3 units of α-rhamnopyranosidase per ml of incubation mixture.

The bioconversion was carried out at a temperature of 25° C. The transformation into desglucodesrhamnoruscin was completed in about 72 hours starting from desglucoruscin and in about 96 hours starting from ruscoside.

The incubation mixture was then centrifuged at 12,100 g for 30 minutes at 40° C. The precipitate was washed with methanol and centrifuged again in the same conditions as above. This step was repeated five times and the supernatants were pooled. The methanol solution was then evaporated under vacuum and the resulting product was triturated to obtain a fine dark yellow powder, containing 20% of desglucodesrhamnoruscin (HPLC assay).

What is claimed is:

1. A method for preparing desglucodesrhamnoruscin which comprises reacting a composition comprising *Ruscus aculeatus* steroid glycosides with one or more hydrolase from *aspergillus niger*, wherein the one or more hydrolase comprises cytolase PCL5, to enzymatically hydrolyze the *Ruscus aculeatus* steroid glycosides and provide a reaction mixture comprising the desglucodesrhamnoruscin, wherein the *Ruscus aculeatus* steroid glycosides comprise a rhamnose-arabinose bond and wherein the one or more hydrolases from *aspergillus niger* is capable of hydrolyzing the rhamnose-arabinose bond.

2. The method of claim 1, wherein the composition comprising *Ruscus aculeatus* steroid glycosides is reacted in an aqueous solution or an ethanol-water solution having up to about 30 percent by volume ethanol.

3. The method of claim 2, wherein the aqueous solution or the ethanol-water solution has a pH of 5.

4. The method of claim 1, wherein the concentration of *Ruscus aculeatus* steroid glycosides comprises from about 5 to about 40 percent w/v of the composition.

5. The method of claim 1, wherein the composition comprising *Ruscus aculeatus* steroid glycosides is reacted with the one or more hydrolases from *aspergillus niger* at a temperature of from 20° C. to 50° C.

6. The method of claim 5, wherein the composition comprising *Ruscus aculeatus* steroid glycosides is reacted with the one or more hydrolases from *aspergillus niger* for from 3 to 7 days.

7. The method of claim 1 further comprising separating the desglucodesrhamnoruscin from the reaction mixture comprising desglucodesrhamnoruscin by centrifugation.

8. The method of claim 2 further comprising washing the desglucodesrhamnoruscin with methanol.

9. The method of claim 1, wherein the *Ruscus aculeatus* steroid glycosides comprise ruscin, desglucoruscin, or ruscoside.

* * * * *